US009488597B2

(12) United States Patent
Hong et al.

(10) Patent No.: US 9,488,597 B2
(45) Date of Patent: Nov. 8, 2016

(54) APPARATUS AND METHODS FOR DETERMINING SURFACE COMPLIANCE FOR A GLASS SURFACE

(75) Inventors: En Hong, Painted Post, NY (US); Philip Robert LeBlanc, Corning, NY (US); Correy Robert Ustanik, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 987 days.

(21) Appl. No.: 13/307,418

(22) Filed: Nov. 30, 2011

(65) Prior Publication Data
US 2013/0135459 A1 May 30, 2013

(51) Int. Cl.
*G01N 21/958* (2006.01)
*G01N 21/94* (2006.01)

(52) U.S. Cl.
CPC ............ *G01N 21/958* (2013.01); *G01N 21/94* (2013.01)

(58) Field of Classification Search
CPC .......................... G01N 21/94; G01N 21/958
USPC ............................ 73/865.8; 348/128; 427/68
See application file for complete search history.

(56) References Cited

U.S. PATENT DOCUMENTS

| 3,338,696 | A | | 8/1967 | Dockerty | .......................... 65/145 |
| 3,682,609 | A | | 8/1972 | Dockerty | .......................... 65/83 |
| 5,694,479 | A | * | 12/1997 | Guering | ............... G01N 21/958 348/130 |
| 5,736,745 | A | | 4/1998 | Nagashima et al. | ...... 250/559.41 |
| 5,969,372 | A | * | 10/1999 | Stavely et al. | ............ 250/559.42 |
| 7,193,698 | B2 | | 3/2007 | Lin et al. | .................... 356/237.3 |
| 7,486,403 | B2 | | 2/2009 | Osaka et al. | ................... 356/496 |
| 2006/0159843 | A1 | * | 7/2006 | Sze et al. | ......................... 427/68 |
| 2007/0013900 | A1 | | 1/2007 | Lin et al. | |
| 2009/0075092 | A1 | * | 3/2009 | Varaprasad | ................... 428/428 |
| 2013/0135459 | A1 | | 5/2013 | Hong et al. | .................... 348/128 |

FOREIGN PATENT DOCUMENTS

| CN | 100483117 C | 4/2009 | .......... G01N 21/896 |
| CN | 101936919 A | 1/2011 | .......... G01N 21/958 |
| EP | 0753736 A2 | 1/1997 | |
| JP | 7-325307 | 12/1995 | .......... G02F 1/1339 |
| JP | 8-210758 | 8/1996 | ............. F25D 21/08 |
| JP | 10-111257 | 4/1998 | ............ G01N 21/88 |
| JP | 2008-89398 A | 4/2008 | .......... G01N 21/958 |
| JP | 2011190039 | 9/2011 | ............. B65G 40/06 |

OTHER PUBLICATIONS

Sep. 28, 2014 Notice on First Office Action issued in Chinese counterpart application No. 201210597659.0 (English translation).

(Continued)

*Primary Examiner* — Hezron E Williams
*Assistant Examiner* — David Z Huang
(74) *Attorney, Agent, or Firm* — Matthew J. Mason

(57) ABSTRACT

A method for determining surface quality for a glass surface is provided. The method includes depositing a pattern of drops over the glass surface using a drop dispensing apparatus. Adjacent drops have a predetermined deposit size and a predetermined deposit spacing. Drop information for the pattern of drops is generated using a vision apparatus. An out-of-parameter condition is detected by analyzing the drop information and an indication of the out-of-parameter condition is provided.

20 Claims, 7 Drawing Sheets

(56) References Cited

OTHER PUBLICATIONS

Akihiko Hattori, Journal of Non-Crystalline Solids, vol. 218, Sep. 2, 1997, pp. 196-204.
T.Young, Phil.Trans.Roy.Soc.London 95,65 (1805).
D.Beysens and C.M.Knobler, Phys.Rev Let. vol. 57 [12] pp. 1433, 1986.
E.L. Decker, B. Frank, Y. Suo, S. Garoff, Colloids and Surfaces A: Physicochemical and Engineering Aspects, vol. 156, Issues 1-3, Oct. 15, 1999, pp. 177-189.
H.Pohlack and S.Wendler, Jenaer Jahrbuch, VEB Carl Zeiss, p. 41, 1948.
H.W.Fox and W.A..Zisman, J.Colloid Sci. 5,514, 1950.

* cited by examiner

APPARATUS AND METHODS FOR DETERMINING SURFACE COMPLIANCE FOR A GLASS SURFACE

FIELD

The present specification generally relates to apparatus and methods for determining surface quality for a glass surface.

BACKGROUND

Glass sheets used as substrates for display applications, e.g., LCDs and organic light emitting diode (OLED) displays, need to have surfaces which are clean and free of particles, films, etc. Extensive washing and drying at the end of the finishing process are often used to clean the glass sheets. Accordingly, efforts have been undertaken to find effective ways of inspecting glass sheet surfaces for determining surface quality.

Extremely thin layers of residue left on glass after washing processes may be measured in nanometers, which do not change the light reflecting, refracting, scattering, polarization enough to be measured using conventional photoelectric sensors. Currently there are no quantitative measurement techniques for large volume high speed surface area cleanliness inspection.

SUMMARY

Several aspects of the present invention are disclosed herein. It is to be understood that these aspects may or may not overlap with one another. Thus, part of one aspect may fall within the scope of another aspect, and vice versa.

Each aspect is illustrated by a number of embodiments, which in turn, can include one or more specific embodiments. It is to be understood that the embodiments may or may not overlap with each other. Thus, part of one embodiment, or specific embodiments thereof, may or may not fall within the ambit of another, or specific embodiments thereof, and vice versa.

Thus, a first aspect of the present disclosure is related to a method for determining surface quality for a glass surface, the method comprising:

depositing a pattern of drops over the glass surface using a drop dispensing apparatus, where adjacent drops have a predetermined deposit size and a predetermined deposit spacing;

generating drop information for the pattern of drops using a vision apparatus;

determining an out-of-parameter condition by analyzing the drop information; and providing an indication of the out-of-parameter condition.

In certain embodiments of the first aspect of the present disclosure, the first outer frame member further comprises detecting presence of the pattern of drops on the glass surface using the vision apparatus.

In certain embodiments of the first aspect of the present disclosure, the drops comprise ink and the drop dispensing apparatus comprises an inkjet printing unit.

In certain embodiments of the first aspect of the present disclosure, the pattern of drops is illuminated using a lighting apparatus.

In certain embodiments of the first aspect of the present disclosure, the lighting apparatus is a dark field lighting apparatus.

In certain embodiments of the first aspect of the present disclosure, the lighting apparatus is a bright field backlighting apparatus.

In certain embodiments of the first aspect of the present disclosure, the drops are each a predetermined volume between about 1 picoliter and about 80 picoliters.

A second aspect of the present disclosure relates to a method for determining surface quality for a glass surface, the method comprising:

depositing one or more patterns of drops over the glass surface using a drop dispensing apparatus, the glass surface having a clean, non-stained area and a stained area, the one or more patterns of drops being deposited over both the non-stained area and the stained area;

generating drop information for the one or more patterns of drops using a vision apparatus; and detecting a difference between drops in the non-stained area and the stained area using a controller based on the drop information.

In certain embodiments of the second aspect of the present disclosure, an indication of an out-of-parameter condition is provided when the difference in size of drops in the non-stained area and the stained area is more than a predetermined amount.

In certain embodiments of the second aspect of the present disclosure, presence of the pattern of drops on the glass surface is detected using the vision apparatus.

In certain embodiments of the second aspect of the present disclosure, the drops comprise ink and the drop dispensing apparatus comprises an inkjet printing unit.

In certain embodiments of the second aspect of the present disclosure, the pattern of drops is illuminated using a lighting apparatus.

In certain embodiments of the second aspect of the present disclosure, the lighting apparatus is a dark field lighting apparatus.

In certain embodiments of the second aspect of the present disclosure, the lighting apparatus is a bright field backlighting apparatus.

In certain embodiments of the second aspect of the present disclosure, the drops are each a predetermined volume between about 1 picoliter and about 80 picoliters.

A third aspect of the present disclosure relates to a surface evaluation apparatus for determining surface quality for a glass surface, the apparatus comprising:

a support assembly that supports a glass sheet;

a drop dispensing apparatus that deposits a pattern of drops over the glass surface supported by the support assembly, where adjacent drops have a predetermined deposit size and a predetermined deposit spacing;

a vision apparatus that generates drop information for the pattern of drops and provides the drop information to a controller;

wherein the controller determines the presence of an out-of-parameter condition based on the drop information.

In certain embodiments of the third aspect of the present disclosure, the vision apparatus includes one or more cameras that detect presence of the pattern of drops on the glass surface.

In certain embodiments of the third aspect of the present disclosure, the drops comprise ink and the drop dispensing apparatus comprises an inkjet printing unit.

In certain embodiments of the third aspect of the present disclosure, a lighting apparatus illuminates the pattern of drops.

In certain embodiments of the third aspect of the present disclosure, the drops are each deposited at a predetermined volume between about 1 picoliter and about 80 picoliters.

Additional features and advantages of the glass substrates and methods for producing the glass substrates will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Corning Incorporated has developed a process known as the Fusion Process (e.g., downdraw process) which forms high quality thin glass sheets that can be used in a variety of devices like flat panel displays. The fusion process is a technique for producing glass sheets that are used in flat panel displays because these glass sheets have surfaces with superior flatness and smoothness when compared to glass sheets produced by other methods. For a detailed description about the fusion process reference is made to U.S. Pat. Nos. 3,338,696 and 3,682,609. The contents of these patents are incorporated herein by reference.

Glass sheets formed using the fusion process or any other suitable glass forming process may be washed at one or more washing stations after their formation. Particles, films and/or coatings can be removed from the glass sheets using various commercial detergent packages either alone or in combination with brush washing and/or ultrasonic cleaning Water-based ultrasonic cleaning or brush cleaning or a combination thereof may be suitable for removing contaminants or other materials from the glass surface. Detergent may be used to remove contamination such as oily materials and particles. An aqueous detergent solution may be used at a concentration of 2-8% and may have an alkaline pH. A cleaning temperature between about 20° C. and 75° C. may be suitable, with higher temperatures normally resulting in more efficient removal of the coating, particles, and organic contaminants. Cleaning time may be between 2 to 15 minutes.

Residue stains on glass surfaces, for example, such as those left behind in the washing processes can cause significant surface tension variations across the glass surface. Surface evaluation apparatus described herein provide for determining surface quality for a glass surface using machine vision and image processing to quantify and interpret the existence of residue stains.

Figure 1:
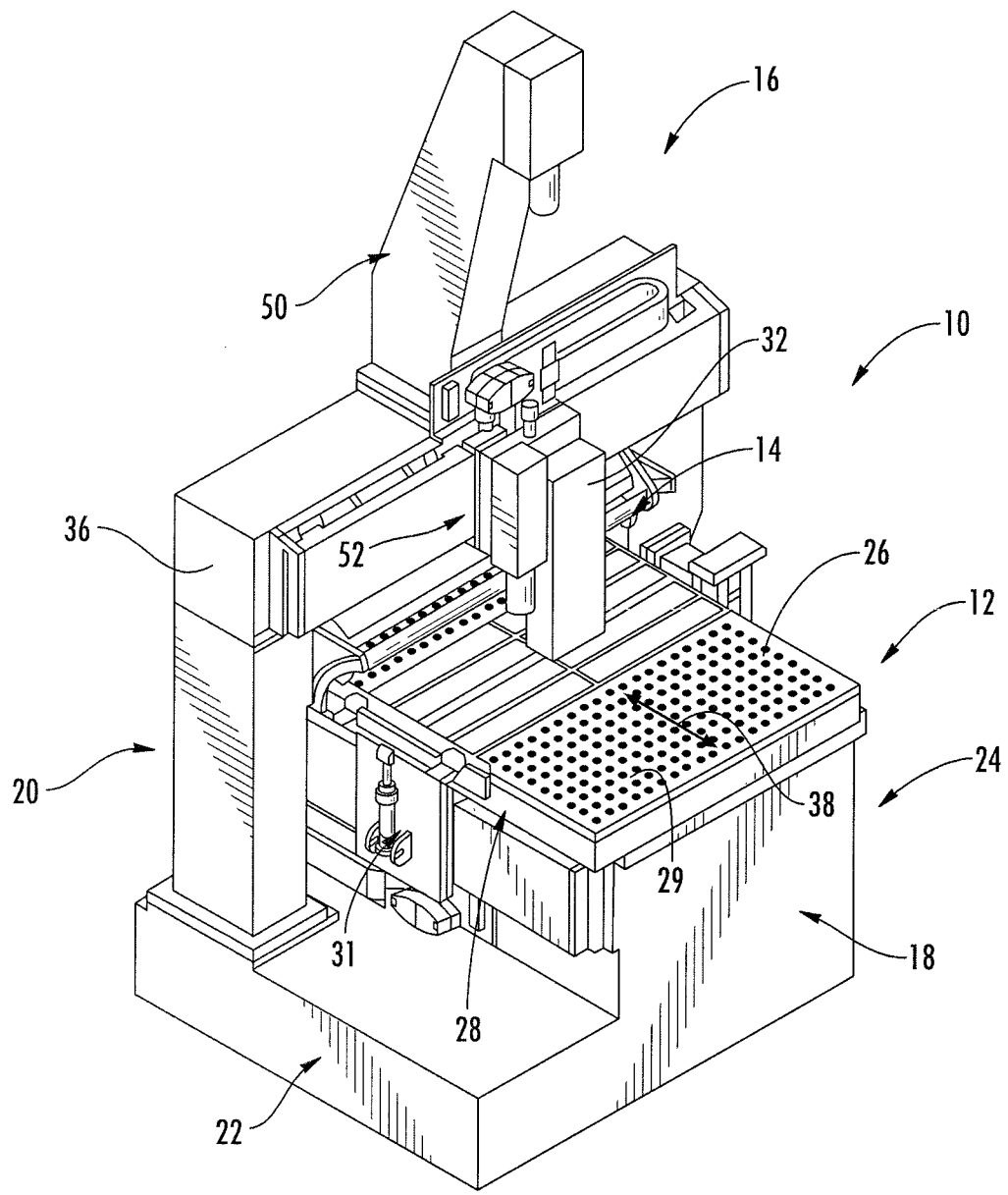
FIG. 1 a perspective view of an embodiment of a surface evaluation apparatus.

Referring to FIG. 1, a surface evaluation apparatus 10 includes a horizontal support assembly 12, a drop dispensing apparatus 14 and a vision apparatus 16. The horizontal support assembly 12 may be supported by a frame and includes a front 18, a rear 20 and sides 22 and 24. A support surface 26 is located between the front 18, rear 20 and sides 22 and 24 and may be formed by a conveying apparatus 28 including, for example, an air table 29 and a moveable glass clamp mechanism 31 or other conveying components such as belts, rollers, and the like capable of moving a glass sheet precisely along the support surface 26. In other embodiments, the support surface 26 may not include any conveying components and may be formed of one or more panels, bars, etc. The horizontal support assembly 12 supports a glass sheet (not shown) beneath the drop dispensing apparatus 14 and the vision apparatus 16 in a flat, horizontal orientation.

The drop dispensing apparatus 14 may include a printing head unit 32, such as an inkjet printing head unit that includes one or more print heads. The printing head unit 32 may be moveable along a cross bar support 36 in a direction transverse to a glass sheet feeding direction (represented by arrow 38). A transverse motor drive may be used for movement of the printing head unit 32 along the cross bar support 36. In some embodiments, such as those employing a conveying apparatus 28, the cross bar support 36 may be stationary while the conveying apparatus 28 including the glass clamp mechanism 31 moves the glass sheet in the feeding direction 38 direction. In other embodiments, the printing head unit 32 may be moveable in the feeding direction. For example, the cross bar support 36 may be movably mounted to the horizontal support assembly 12 in tracks. Air from the air table 29 may be used to maintain space between the glass sheet and the support surface 26. A motor or other actuator may be used to move the cross bar support 36 and printing head unit 32 in the feeding direction 38. A screw drive mechanism, for example, may be utilized for controlling movement of the cross bar support 36 and/or the printing head unit 32.

The printing head unit 32 may be provided with controls that allow for the operation of the printing heads to selectively print patterns of drops onto the glass surface of the glass sheet. Any suitable print propulsion method may be used, such as thermal DOD (drop-on-demand) inkjet and piezoelectric DOD inkjet technologies. The drives for the print head unit 32 and the conveying apparatus 28 and operation of the printing heads may be program controlled to print patterns of drops in predetermined locations on the glass surface of the glass sheet by a controller 44 (FIG. 9; e.g., a computer), which includes a memory for storing programmed patterns, machining control programs and real time data regarding the nature and longitudinal and transverse position of the glass sheet 106 (FIG. 2) on the support surface 26.

The printing head unit 32 may deposit ink onto the glass sheet using piezoelectric DOD inkjet technology. Drop sizes may range from about 1 to about 80 picoliters, such as from about 14 to about 42 picoliters, with a spacing of about 100 to about 200 microns between adjacent drops. Thickness of the glass sheets 106 may be up to about 50 mm. Relatively large glass sheets 106 may be used, such as up to about 3.5 m×3.5 m or more. Various commercially available printing head units may be used such as available from Cannon, Inc. and Xaar plc, as examples.

The vision apparatus 16 may be used to generate drop information for the pattern of drops deposited by the printing head unit 32. As used herein, the term "drop" used to generate the drop information includes wet drops, dry drops and the continuum of drop formations between wet and dry drops. Details of the vision apparatus 16 are described in greater detail below. The drop information may include one or more of pattern information, drop location information and drop size information. The vision apparatus 16 may be connected to the controller 44 that includes logic for analyzing the drop information.

Figure 2:
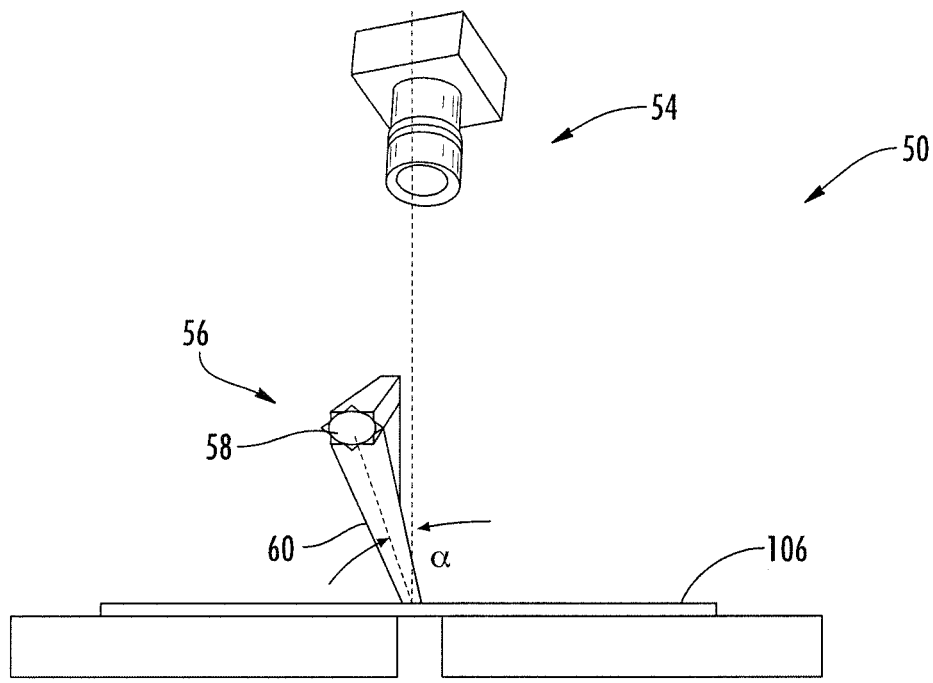
FIG. 2 is an illustration of an embodiment of a macro vision camera apparatus for use in the surface evaluation apparatus of FIG. 1.

In one exemplary embodiment, the vision apparatus 16 may include one or more camera apparatus, such as a macro vision camera apparatus 50 and a micro vision camera apparatus 52. Referring to FIG. 2, the macro vision camera apparatus 50 may include one or more line scan camera 54 and dark field lighting apparatus 56. The dark field lighting apparatus 56 may include a line light source 58 on the same side of the glass sheet 106 as the line scan camera 54 that directs a beam of light 60 toward the glass sheet 106 at an oblique angle (e.g., an angle a of between about 0 to about 10 degrees, such as about 5 degrees) to vertical (or at an angle to the vision axis of the camera). The macro vision camera apparatus 50 may be used to identify regions of interest in the drop patterns over only a portion or portions of the glass surface of the glass sheet 106. These regions of interest may be indicated using light scattering and/or reflecting changes across the drop pattern caused by variations in surface chemistry across the surface of the glass sheet 106. The line scan camera 54 and dark field lighting apparatus 56 may be selected to visualize and illuminate a region spanning the entire width of the glass surface of the glass sheet 106 for the purpose of identifying these regions of interest. Multiple line scan cameras 54 may be used. In some embodiments, only feed direction movement of the glass sheet 106 is needed to visualize the entire glass surface of the glass sheet 106. However, the macro vision camera apparatus 50 may utilize other scanning patterns, such as raster scanning of the glass surface.

Figure 3:
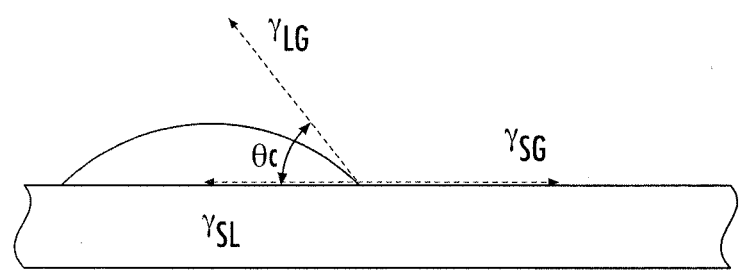
FIG. 3 illustrates Young's Equation for determining contact angle of a fluid drop on a rigid, flat surface.

Referring to FIG. 3, the line scan camera 54 can be used to determine the regions of interest that occur due to the chemical variations on the glass surface of the glass sheet 106, which result in changes in shape of the drops. FIG. 3 illustrates the contact angle of a liquid drop (e.g., an ink drop) wetted to a rigid solid surface (e.g., of the glass sheet).

When a drop of liquid is placed on such a surface, the characteristic contact angle θc is formed and can be determined by Young's Equation $$\gamma_{SG} = \gamma_{SL} + \gamma_{LG} \cos \theta c,$$

where $\gamma_{SL}$, $\gamma_{LG}$, and $\gamma_{SG}$ are the interfacial tensions between the solid and the liquid, the liquid and the vapor, and the solid and the vapor, respectively. The equilibrium contact angle that the drop makes with the surface is denoted by θc. Young's Equation can be used to predict the contact angle of a liquid drop on a solid surface from knowledge of the three surface energies involved.

Figure 4:
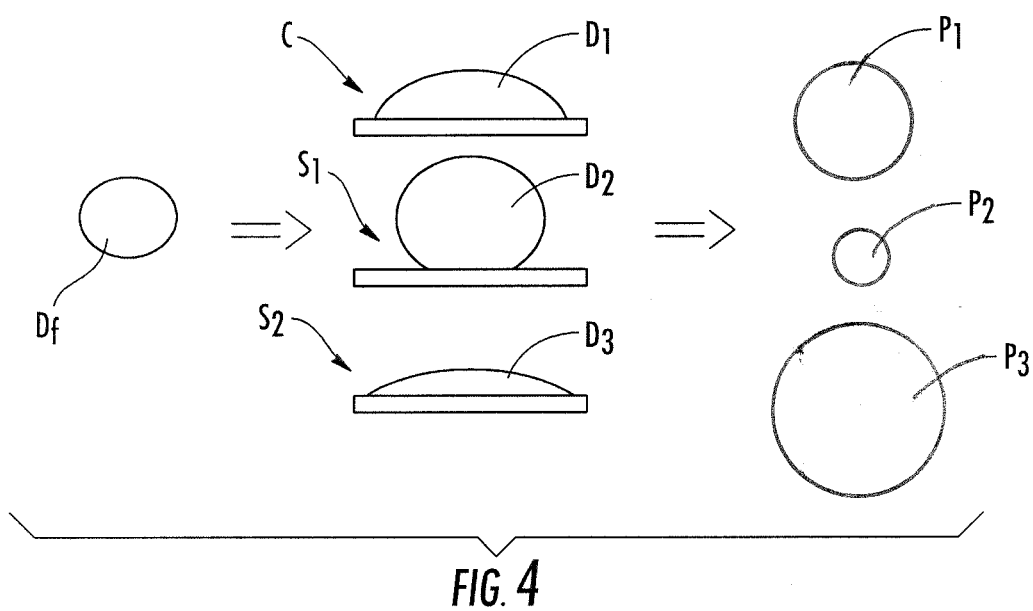
FIG. 4 illustrates examples of different drop shapes on a rigid, flat surface resulting from a free space drop due to variations of surface chemistry on the glass surface.

FIG. 4 illustrates examples of different drop shapes from a free space drop $D_f$ due to variations of surface chemistry on a glass surface. For a clean glass surface region C, a drop $D_1$ would have a predictable shape including contact angle and footprint $P_1$. $S_1$ illustrates a region where drop $D_2$ is less wet-able on the stain than on clean glass, having a lesser area footprint $P_2$ and a greater contact angle comparing to drop $D_1$. On the opposite, $S_2$ illustrates a region where drop $D_3$ is more wet-able on the stain than on clean glass, having a greater area footprint $P_3$ and a lower contact angle comparing to $D_1$. However, both cases can generate the morphology contrast which is needed in the inspection and quantification. These variations of numerous drops over one or more regions, when compared to clean glass surface regions C can be detected using the macro vision camera apparatus 50. In some embodiments, there can be between about 10 percent and 75 percent diameter difference depending, at least in part, on the ink formulation and the stain type.

Figure 5:
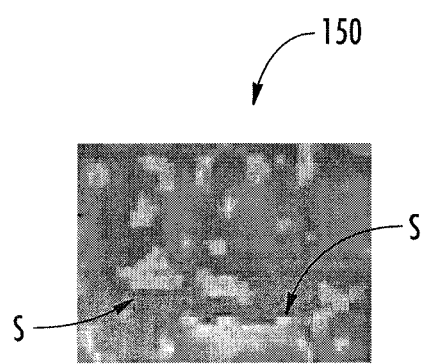
FIG. 5 is a dark field, low magnification image, which is exemplary of an image that may be acquired using a macro vision camera apparatus of the surface evaluation apparatus of FIG. 1.
Figure 7:
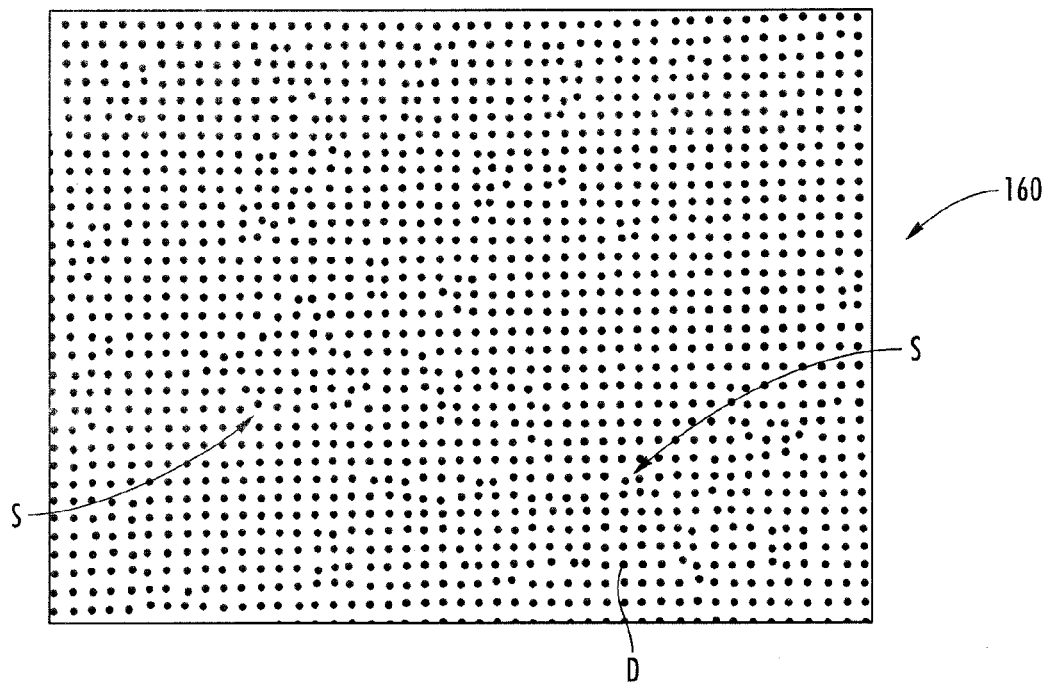
FIG. 7 is a bright field microscopy image, which is exemplary of an image that may be acquired using a micro vision camera apparatus of the surface evaluation apparatus of FIG. 1.

Referring to FIG. 5, a dark field, low magnification image 150 is illustrated, which is exemplary of an image that may be acquired using the macro vision camera apparatus 50 of a pattern of drops (see the microscopy image 160 of FIG. 7 showing the pattern of drops). The low magnification image 150 may only be a portion of the total image captured by the macro vision camera apparatus 50. Due in part to the differences in light scattering and reflecting between the clean and stained regions, the stained regions S show as relatively bright areas in the image 150 and determine the surface quality of the glass surface by, for example, providing an indication of a potential out-of-parameter condition indicated by the light scattering and/or reflecting properties of the drops within these regions of interest.

Figure 6:
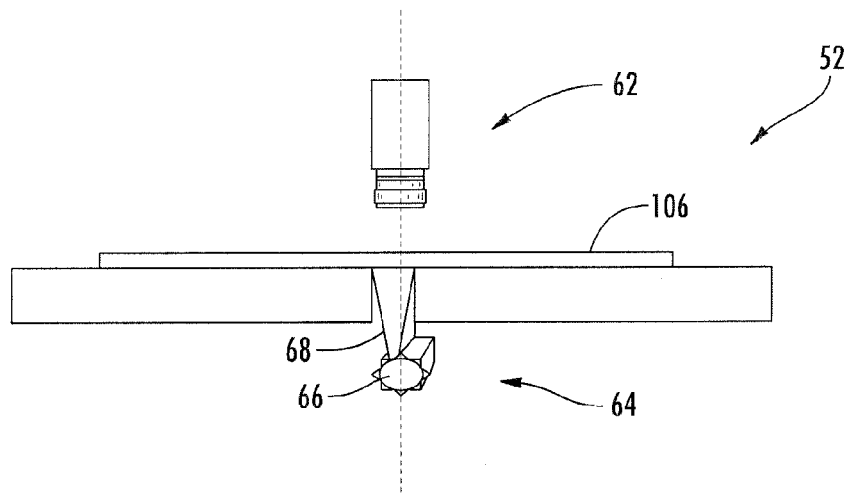
FIG. 6 is an illustration of an embodiment of a micro vision camera apparatus for use in the surface evaluation apparatus of FIG. 1.

Once presence of the stained regions S are identified on the glass surface of the glass sheet 106 within the pattern of drops, the micro vision camera apparatus 52 may visit these known locations with a higher magnification. Referring to FIG. 6, the micro vision camera apparatus 52 may include one or more area scan camera 62 and bright field backlighting apparatus 64. The bright field backlighting apparatus 64 may include a line light source 66 on a side of the glass sheet 106 opposite the area scan camera 62 that directs a beam of light 68 through an opening in the horizontal support surface 26 and toward the glass sheet 106 at a vertical direction (or along the vision axis of the area scan camera 62). The micro vision camera apparatus 52 may be used for high resolution confirmation of drop size and shape. The area scan camera 62 and bright field backlighting apparatus 64 may be selected to visualize and illuminate a relatively small area of discrete drops spanning only a portion of the width of the glass surface of the glass sheet 106. In some embodiments, both transverse and feed direction movement of the micro vision camera apparatus 52 and/or the glass sheet 106 are needed to visualize the patterns of drops located over the glass surface of the glass sheet 106. In one embodiment, the area scan camera 62 may be connected to the printing head unit 32 for movement therewith.

Figure 8:
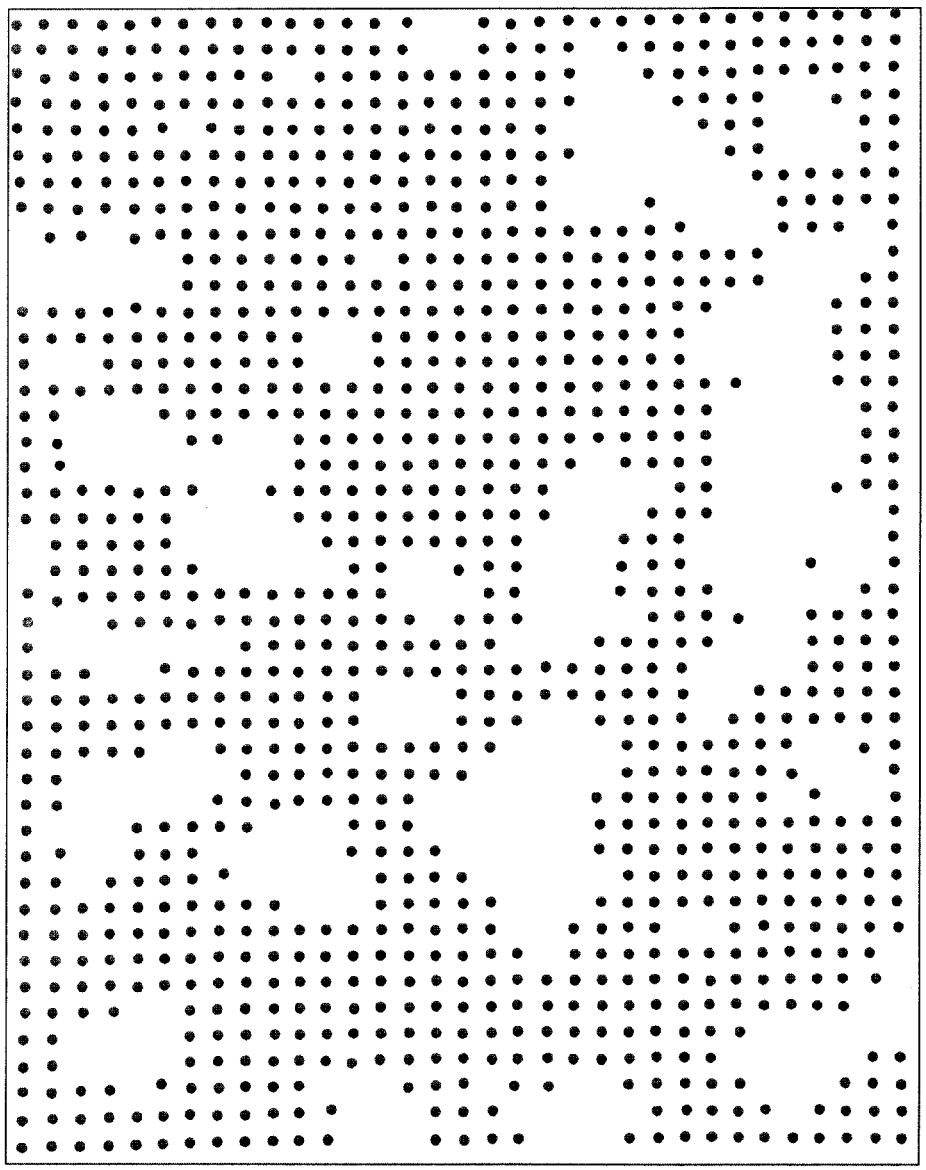
FIG. 8 illustrates the image of FIG. 7 filtered by an image processing algorithm, which highlights regions of interest.

Referring to FIG. 7, a bright field microscopy image 160 of the region captured by the low magnification image 150 is illustrated, which is exemplary of an image that may be acquired using the micro vision camera apparatus 52. The image 160 may be a filtered image to form the illustrated binary image. As can be seen within the exemplary regions S, clusters of the drops D can be seen with differences in size, shape and/or spacing, which can be detected by the micro vision apparatus 52. FIG. 8 illustrates the image 160 further filtered by an image processing algorithm that eliminates drop images based on preselected criteria such as drop size, drop shape, drop intensity, which highlights the regions of interest S, determining the surface quality of the glass surface by, for example, indicating an out-of-parameter condition. The image 160 is filtered to remove drops falling outside the preselected criteria such that drop in clean regions remain while drops in stained regions are removed. The filtering may be accomplished by the controller 44 or other computing apparatus.

Figure 9:
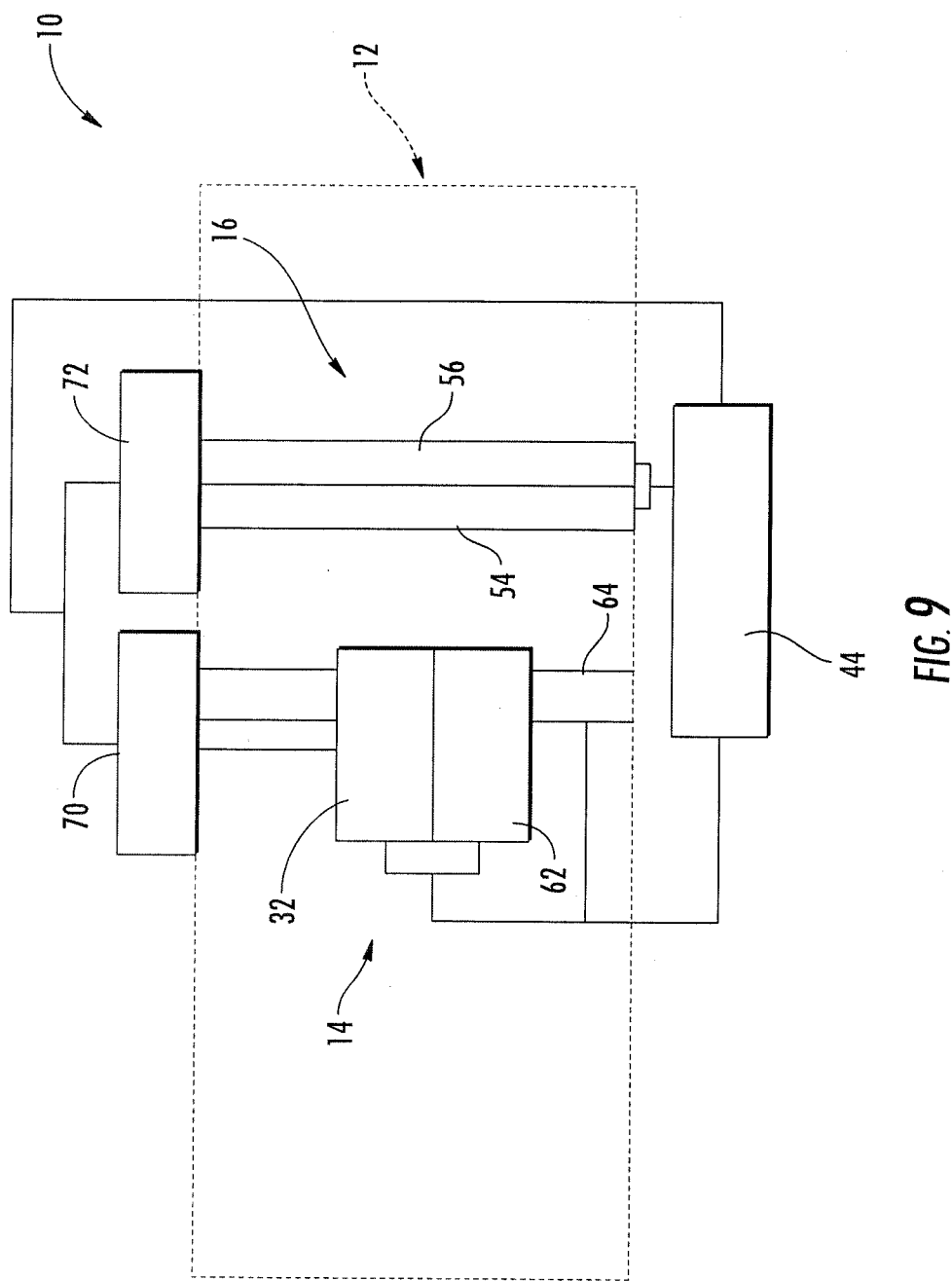
FIG. 9 is an illustration of the surface evaluation apparatus of FIG. 1.

Referring to FIG. 9, a schematic illustration of the surface evaluation apparatus 10 includes the horizontal support assembly 12, the drop dispensing apparatus 14 including the printing head unit 32 and the vision apparatus 16 including the line scan camera 54 and the area scan camera 62. The area scan camera 62 and the printing head unit 32 may both utilize the same drive apparatus 70 (e.g., including the cross bar support 36 of FIG. 1). The line scan camera 54 may utilize the same drive apparatus 70 or a different drive apparatus 72 or no drive apparatus. In some embodiments, the drive apparatus 70 and 72 may be part of the same drive apparatus. In some embodiments, the drive apparatus 72 may be associated with the conveying apparatus 28. The dark field lighting apparatus 56 may be associated with the line scan camera 54 and the bright field backlighting apparatus 64 may be associated with the area scan camera 62. As indicated above, the dark field lighting apparatus 56 may be located on the same side of the glass sheet 106 and the bright field backlighting apparatus 64 may be located on a side of the glass sheet 106 that is opposite the area scan camera 62.

The controller 44 (e.g., a computer) controls operation of the drive apparatus 70, 72, the printing head 32 and the vision apparatus 16. The controller 44 may also receive information back from the printing head 32 and the vision apparatus 16. The controller 44 may also receive information from various sensors, for example, that are used to locate the glass sheet 106 on the horizontal support surface 20. Rulers and stoppers may also be used at predetermined positions on the horizontal support surface 20 to detect marginal limits of the glass sheet 106. Suction cups or other mechanisms or materials may be used to firmly grip the glass sheet 106.

Figure 10:
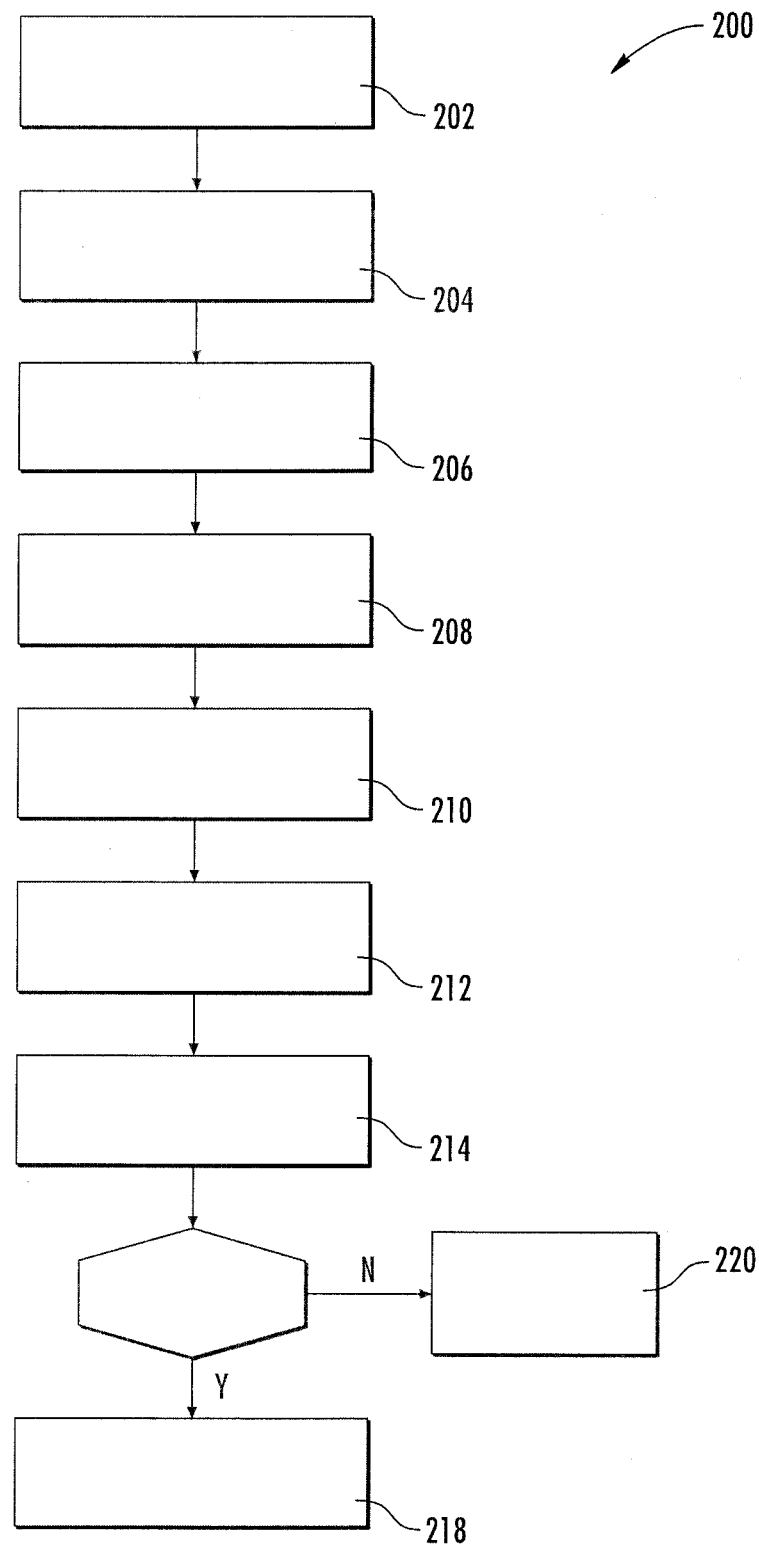
FIG. 10 illustrates an embodiment of a method for determining surface quality for a glass surface using the surface evaluation apparatus of FIG. 1.

Referring to FIG. 10, a method 200 for determining surface quality for a glass surface includes positioning the glass sheet 106 on the horizontal support surface 20 at step 202. The positioning can be done manually or automatically, for example, using a robot end effector, conveyor, etc. At step 204, a pattern of drops are deposited on the glass surface of the glass sheet 106 using the printing head unit 32. The controller 44 can instruct the printing head unit 32 to deposit the drops having a predetermined size and a predetermined spacing from each other. The pattern can be one of many forms, such as in a matrix having columns and rows of the drops. At step 206, the line scan camera 54 of the vision apparatus 16, using the dark field lighting apparatus 56, detects the presence of a region of interest on the glass sheet 106 using contrast between the stained and clean regions and sends pattern and location information to the controller 44. The controller 44, using the pattern and location information, may direct the area scan camera 62 to the region of interest at step 208. At step 210, the area scan camera 62 of the vision apparatus 16, using the bright field backlighting apparatus 64, generates drop information, which may include one or more of drop size information, drop shape information and pattern information including pattern spacing and light scattering and/or reflecting information. In other embodiments, the macro vision system 50 may be used to generate the drop information without use of the micro vision system 52. The drop information may be sent to the controller 44 at step 212. At step 214, the controller 44 analyzes the drop information. In some embodiments, the controller 44 may compare regions of drop information. In some embodiments, the controller 44 may compare the drop information to a predetermined drop profile saved in memory. If the drop information falls outside the predetermined drop profile and/or contrasts with other regions of the pattern of drops, the controller 44 may provide an indication of an out-of-parameter condition at step 218. If the drop information falls within the predetermined drop profile and/or does not contrast with other regions of the pattern of drops, the controller 44 may provide a within parameter indication at step 220. Any suitable indications may be provided, such as lights, sounds, reports and combinations thereof.

A number of fluid materials may be used for providing the drops. Inks having a relatively high surface tension (e.g., greater than about 50 dyne/cm) may be used. Inks having a surface tension that is much different from the surface tension of the stain can magnify the contrast between regions of the pattern. Higher surface tension drop materials can generate more morphology contrast between drop sizes. Inks having a high optical density may also be used, which can create a greater contrast between the drop image and surrounding areas. Other parameters to consider may include jettability of the fluid, viscosity of the fluid and surface properties of the sheet material.

The above-described surface evaluation apparatus 10 may be used to deposit predetermined surface tension drops in high spatial density (100-200 micron spacing) on an entire glass surface precisely to evaluate cleanliness of the glass surface after washing based on regional contrasts within a pattern of the drops. This is due to the difference in surface tension between clean and stained areas of the glass surface. A contrast mechanism is provided based on this surface tension difference. The size, morphology, scattering and reflecting contrast and spacing of the drops can be quantified using the vision apparatus and image processing of the surface evaluation apparatus 10.

In some embodiments, one or more coatings may be applied to the glass sheets 106 before and/or after washing. In some instances, the coatings may be removed during the washing process, the success of which can be determined using the surface evaluation apparatus 10. While evaluation of cleanliness of a glass surface may be accomplished using the surface evaluation apparatus 10, the above surface evaluation apparatus 10 and methods may be used to characterize surface chemical composition generally. As one example, the surface evaluation apparatus 10 may be used to determine the suitability of particular surface coatings (e.g., for adhering to a surface). The methods and apparatus described herein can also determine variations in surface roughness across some surfaces. Such determinations may be accomplished, at least in part, through analysis of surface energy of various glass surfaces. The above-described systems and processes may also be suitable for non-glass surfaces, such as some metal and plastic surfaces.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modification and variations come within the scope of the appended claims and their equivalents.

What is claimed is:

1. A method for determining surface quality for a glass surface, the method comprising:
    depositing a pattern of drops over a first portion and a second portion of the glass surface using a drop dispensing apparatus after the first portion and the second portion of the glass surface undergo a cleaning operation, where adjacent drops have a predetermined deposit size and a predetermined deposit spacing;
    generating a first output of drop information for the pattern of drops on the first portion of the glass surface and a second output of drop information for the pattern of drops on the second portion of the glass surface using a vision apparatus;
    determining an out-of-parameter condition using a controller analyzing the first output of drop information for the pattern of drops on the first portion of the glass surface and the second output of drop information for the pattern of drops on the second portion of the glass surface caused by surface tension variations across the first portion and the second portion of the glass surface resulting from the cleaning operation; and
    providing an indication of the out-of-parameter condition using the controller, for determining the surface quality for the glass surface.

2. The method of claim 1 further comprising detecting presence of the pattern of drops on the glass surface using the vision apparatus.

3. The method of claim 1, wherein the drops comprise ink and the drop dispensing apparatus comprises an inkjet printing unit.

4. The method of claim 1 further comprising illuminating the pattern of drops using a lighting apparatus.

5. The method of claim 4, wherein the lighting apparatus is a dark field lighting apparatus and the drop information includes light reflection and scattering information from the pattern of drops.

6. The method of claim 4, wherein the lighting apparatus is a bright field backlighting apparatus and the drop information includes drop size and shape information.

7. The method of claim 1, wherein the drops are each a predetermined volume from 1 picoliter up to 80 picoliters.

8. The method of claim 1, wherein the step of determining the out-of-parameter condition using the controller includes comparing the first output of drop information and the second output of drop information.

9. The method of claim 1, wherein the step of determining the out-of-parameter condition using the controller includes comparing the first output of drop information and the second output of drop information to a predetermined drop profile.

10. The method of claim 9, wherein a set of one or more portions of at least one of the first output of drop information and the second output of drop information that fall outside of the predetermined drop profile are representative of the out-of-parameter condition, wherein a set of one or more portions of at least one of the first output of drop information and the second output of drop information that fall within the predetermined drop profile are representative of a within parameter condition, and wherein the predetermined drop profile comprises a contact angle of a drop against the glass surface.

11. The method of claim 1, further comprising:
    determining a within parameter condition using a controller analyzing the first output of drop information for the pattern of drops on the first portion of the glass surface and the second output of drop information for the pattern of drops on the second portion of the glass surface;
    providing an indication of the within parameter condition using the controller, for determining the surface quality for the glass surface; and
    generating an image using the controller in which the indication of the out-of-parameter condition is removed from the image and the indication of the within parameter condition remains in the image.

12. A surface evaluation apparatus for determining surface quality for a glass surface, the apparatus comprising:
    a support assembly that supports a glass sheet, the glass sheet comprising the glass surface, and the glass surface having a first portion and a second portion;
    a drop dispensing apparatus that deposits a pattern of drops over the first portion of the glass surface supported by the support assembly and the second portion of the glass surface supported by the support assembly after the first portion and the second portion of the glass surface undergo a cleaning operation, where adjacent drops have a predetermined deposit size and a predetermined deposit spacing;
    a vision apparatus that generates a first output of drop information for the pattern of drops over the first portion of the glass surface and a second output of drop information for the pattern of drops over the second portion of the glass surface and provides the first output of drop information and the second output of drop information to a controller;
    wherein the controller determines the presence of an out-of-parameter condition based on the first output of drop information and the second output of drop information caused by surface tension variations across the first portion and the second portion of the glass surface resulting from the cleaning operation, the presence of the out-of-parameter condition determining the surface quality for the glass surface.

13. The apparatus of claim 12, wherein the vision apparatus includes one or more cameras that detect presence of the pattern of drops on the glass surface.

14. The apparatus of claim 12, wherein the drops comprise ink and the drop dispensing apparatus comprises an inkjet printing unit.

15. The apparatus of claim 12 further comprising a lighting apparatus that illuminates the pattern of drops.

16. The apparatus of claim 12, wherein the drops are each deposited at a predetermined volume from 1 picoliter up to 80 picoliters.

17. The apparatus of claim 12, wherein the controller determines the presence of the out-of-parameter condition by comparing the first output of drop information and the second output of drop information.

18. The apparatus of claim 12, wherein the controller determines the presence of the out-of-parameter condition based on the first output of drop information and the second output of drop information and comparing the first output of drop information and the second output of drop information to a predetermined drop profile.

19. The apparatus of claim 18, wherein a set of one or more portions of at least one of the first output of drop information and the second output of drop information that fall outside of the predetermined drop profile are representative of the out-of-parameter condition, wherein a set of one or more portions of at least one of the first output of drop information and the second output of drop information that fall within the predetermined drop profile are representative of a within parameter condition, and wherein the predetermined drop profile comprises a contact angle of a drop against the glass surface.

20. The apparatus of claim 12, further comprising:
wherein the controller determines the presence of a within parameter condition based on the first output of drop information and the second output of drop information, the presence of the within parameter condition determining the surface quality for the glass surface; and
wherein the controller generates an image in which the indication of the out-of-parameter condition is removed from the image and the indication of the within parameter condition remains in the image.

* * * * *